US00PP35188P2

(12) United States Plant Patent
Van Dijk

(10) Patent No.: US PP35,188 P2
(45) Date of Patent: May 23, 2023

(54) ***ANTHURIUM* PLANT NAMED 'AN2884386'**

(50) Latin Name: ***Anthurium andraeanum* L.**
Varietal Denomination: AN2884386

(71) Applicant: ANTHURA B.V., Bleiswijk (NL)

(72) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/803,689

(22) Filed: Oct. 11, 2022

(51) Int. Cl.
*A01H 5/02* (2018.01)
*A01H 6/10* (2018.01)
*A01H 6/00* (2018.01)

(52) U.S. Cl.
USPC ..... Plt./365
CPC ..... *A01H 6/10* (2018.05); *A01H 6/00* (2018.05)

(58) Field of Classification Search
USPC ..... Plt./365
CPC ..... A01H 5/02
See application file for complete search history.

*Primary Examiner* — Kent L Bell
(74) *Attorney, Agent, or Firm* — Jondle & Associates, P.C.

(57) ABSTRACT

A new *Anthurium* plant named 'AN2884386' particularly distinguished by having weakly blistered and medium glossy, white with red tips, orbicular-cordate, and durable spathes that retain the original color for a very long period of time, green, deltoid, durable leaves, purplish-red spadices with red tips, early and rich flowering continuously throughout the year, and a plant height of 33.0 cm to 38.0 cm is disclosed.

3 Drawing Sheets

Genus and species: *Anthurium andraeanum* L.
Variety denomination: 'AN2884386'.

BACKGROUND OF THE NEW PLANT

The present invention comprises a new and distinct variety of *Anthurium*, botanically known as *Anthurium andraeanum* L., and hereinafter referred to by the variety name 'AN2884386'. The new *Anthurium* plant is a product of a planned breeding program conducted by the inventor in Bleiswijk, the Netherlands. The objective of this breeding program was to create a new plant with a height of 33.0 cm to 38.0 cm having weakly blistered and medium glossy, white with red tips, orbicular-cordate, and durable spathes.

The new variety originated from a cross-pollination made in February 2013 in Bleiswijk, the Netherlands. The female parent was a light pink *Anthurium* pot plant designated '12870-01' (unpatented), and the male parent was a pink *Anthurium* pot plant designated 'ANTHFOFUN' (U.S. Plant Pat. No. 30,527).

A single plant was selected from the progeny of the stated cross in December 2014. Asexual reproduction of the new variety by tissue culture in 2018 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Nov. 19, 2021 (Application no. 2021/2979), by Applicant who obtained the subject matter disclosed directly from the inventor. 'AN2884386' has not been made publicly available or sold anywhere in the world prior to the effective filing date of this application with the exception of sales or disclosures made one year or less before the effective filing date of this claimed invention by Applicant who obtained 'AN2884386' directly from the inventor.

SUMMARY OF THE INVENTION

The following are the most outstanding and distinguishing characteristics of this new variety when grown under normal horticultural practices in Bleiswijk, the Netherlands:

1) Weakly blistered, medium glossy, white with red tips, and orbicular-cordate spathes;
2) Purplish-red spadices with red tips;
3) Green, deltoid leaves;
4) Petioles and peduncles of mature leaves and spathes, anthocyanin coloration is strong;
5) Spathes shape in cross section of middle zone is straight; and
6) Plant is rich in making shoots.

DESCRIPTION OF THE PHOTOGRAPHS

This new *Anthurium* plant is illustrated by the accompanying photographs which show the overall plant habit including blooms, buds, and foliage of the plant; the colors shown are as true as can be reasonably obtained by conventional photographic procedures. The photographs are of a 34-week-old plant grown in a greenhouse in Bleiswijk, the Netherlands, in June 2022. Colors in the photographs may differ from the color values cited in the detailed botanical description, which accurately describe the actual colors of the new variety.

DESCRIPTION OF THE NEW VARIETY

Figure 1:
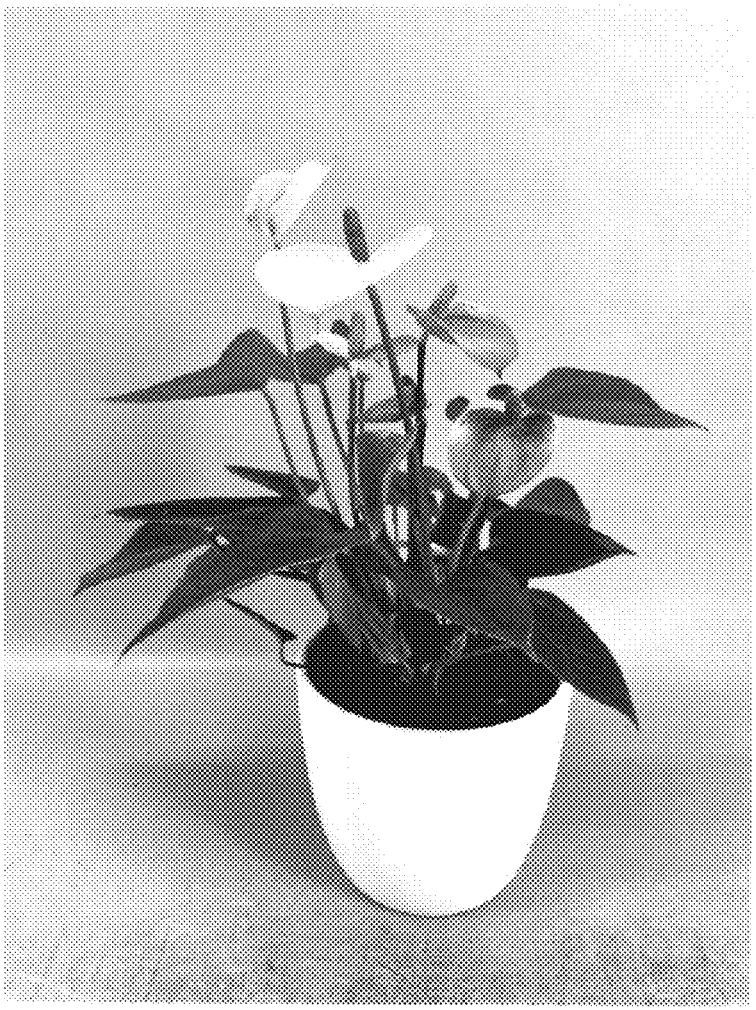
FIG. 1 shows the overall plant habit, including blooms, buds, and foliage.
Figure 2:
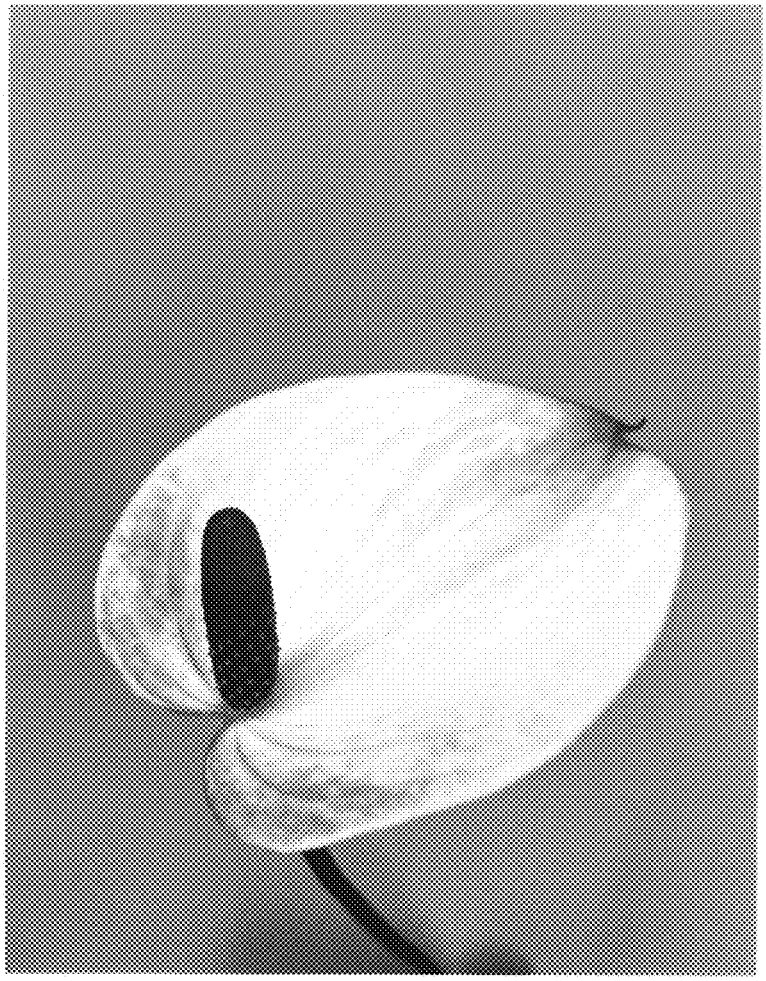
FIG. 2 shows a close-up of the mature spathe.
Figure 3:
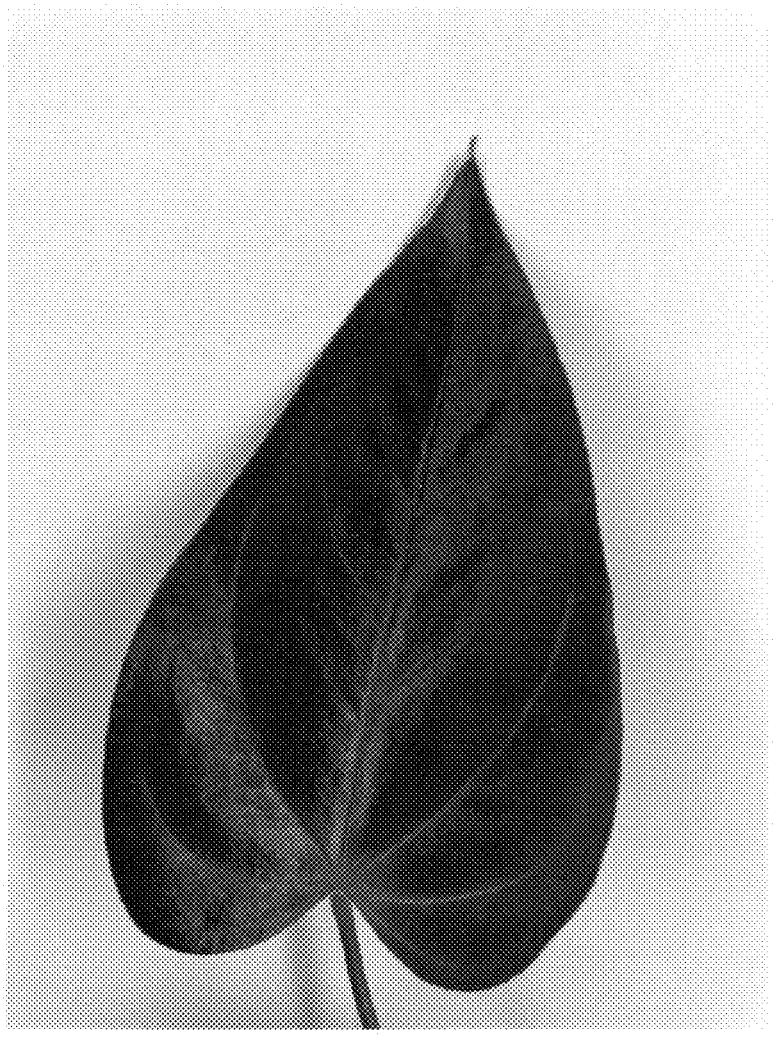
FIG. 3 shows a close-up of the upper leaf blade surface.

The following detailed description sets forth the distinctive characteristics of 'AN2884386'. The data which define these characteristics were collected from asexual reproductions carried out in Bleiswijk, the Netherlands. The plant history was taken on 34-week-old plants which were planted from tissue culture in 12-centimeter (diameter) pots and grown in a glass greenhouse between 19° C. and 24° C. Observations were made in June 2022. Color readings were taken under 5000 lux natural light in the greenhouse. Color references are primarily to The R.H.S. Colour Chart of The Royal Horticultural Society of London (RHS) (2015).

DETAILED BOTANICAL DESCRIPTION

Classification:

*Family.*—Araceae.

*Botanical.*—*Anthurium andraeanum* L.

*Common name.*—*Anthurium.*

*Denomination.*—'AN2884386'.

Parentage:

*Female parent.*—*Anthurium* plant '12870-01' (unpatented).

*Male parent.*—*Anthurium* plant 'ANTHFOFUN' (U.S. Plant Pat. No. 30,527).

Plant:

*Propagation.*—Tissue culture.

*Root description.*—Fleshy-creamy (RHS 158C) colored roots with a touch of light pink shade (RHS 38C), and small hairy lateral roots having yellow (RHS 6B) colored root tips.

*Time to produce a finished flowering plant.*—32 to 36 weeks after planting in a 12-cm (diameter) pot.

*Growth habit.*—Upright.

*Height* (*measured from soil, including inflorescence*).—33.0 cm to 38.0 cm.

*Width* (*measured from leaf tips*).—30.0 cm to 33.0 cm.

Leaves:

*Immature leaves.*—Length: 8.0 cm to 11.0 cm. Width: 5.5 cm to 6.5 cm. Color: Upper surface: RHS 146A. Lower surface: RHS 146B. Texture (both upper and lower surfaces): Glossy, leathery, and thin.

*Mature leaves.*—Length (fully expanded): 12.0 cm to 14.0 cm. Width: 7.5 cm to 8.5 cm. Shape: Deltoid. Apex: Cuspidate. Base: Cordate. Leaf blade angle with the petiole: Between 110 degrees and 130 degrees. Leaf margin: Entire. Color: Upper surface: RHS 147A. Lower surface: RHS 146B. Texture (upper surfaces): Leathery and thick. Texture (lower surface): Glossy, leathery, and thick. Venation: Pinnate veining; the mid-vein and primary veins (the veins that radiate out from the junction of petiole and leaf) protrude at the underside of the leaf blade. Venation color: Upper surface: RHS 183B at the base and RHS 144A toward the tips. Lower surface: RHS 144B.

*Lobes.*—Present. Arrangement: Leaf blade has two lobes extending past the petiole. The lobes are non-touching. Length of lobes of mature leaf blades: 0.5 cm to 1.0 cm. Width of lobes of mature leaf blades: 2.0 cm to 3.0 cm. Distance from petiole/leaf junction to highest point on lobes of mature leaf blades: 1.0 cm to 2.0 cm.

*Petiole.*—Cross-section: Round. Diameter: 0.2 cm to 0.3 cm. Length: 10.0 cm to 13.0 cm for a mature leaf size. Color: Mature leaf: RHS 144B with a red shade (RHS 183A); when mature leaf ages, petiole turns from green (RHS 144B) to red (RHS 183A). Immature leaf: RHS 144B; sometimes older leaves turn to dark reddish-orange (RHS 178B). Cataphyll color surrounding the petiole: Outside: RHS 145B with red (RHS 182A) tips. Inside: RHS 145C.

*Geniculum.*—Length: 1.0 cm to 1.5 cm. Width: 0.3 cm to 0.4 cm. Color: RHS 144C.

Inflorescence:

*Arrangement.*—Single.

*Flowering habit* (*length of flowering season*).—Continuous.

*Number of inflorescences per plant.*—6 to 8.

*Fragrance.*—Absent.

*Longevity of inflorescence on plant.*—Over a year.

Spathe:

*Buds.*—The spathe is tightly rolled around the spadix and extrudes from the peduncle sheath. After the spathe is fully opened, the peduncle elongates some extra centimeters.

*Arrangement.*—Spathe angle with the peduncle is between 90 degrees and 100 degrees; the spathe stands on a wiry peduncle about 4.0 cm to 7.0 cm above the foliage.

*Shape.*—Orbicular Cordate.

*Apex.*—Abruptly acuminate.

*Base.*—Cordate.

*Texture.*—Weakly blistered and medium glossy.

*Margin.*—Undulated.

*Size.*—Length: 6.5 cm to 7.5 cm. Width: 6.5 cm to 7.5 cm.

*Lobes.*—Absent.

*Color.*—Just fully open: Upper surface: Red margin at the base (RHS N45D); light yellow-green lobes (mix of RHS 145B and RHS 145C); white towards the tips (RHS 155B) with red (RHS N45B) tips. Lower surface: RHS 155B with red margin (RHS N45D) toward the tips. This white color, when the spathe becomes older, turns to pink (RHS 50B).

Peduncle:

*Shape.*—Erect.

*Cross-section.*—Round.

*Length.*—16.0 cm to 19.0 cm.

*Diameter.*—0.3 cm to 0.4 cm.

*Color.*—RHS 144B with a reddish-brown shade (RHS 175A).

Flowering time:

*General.*—One small, rooted, untreated tissue culture plant of 8.0 cm tall will flower, depending on the season, after 32 to 36 weeks and 6 to 7 blossoms appear. More blossoms appear after some additional weeks so that a full flowering and commercial plant will have 7 to 8 white spathes. Smaller blossoms may occur on immature plants.

Spadix:

*Size.*—Length: 2.0 cm to 2.5 cm (depending on flower size). Width (at apex): 0.5 cm to 0.6 cm. Width (at base): 0.6 cm to 0.7 cm.

*Shape.*—Columnar.

*Angle of spadix tip with peduncle.*—160 degrees to 170 degrees.

*Texture.*—When the spathe is unfurling, the spadix is smooth. When the spadix matures, small stigmata protrude. The stigmata are evenly distributed around the spadix. The spadix matures from base to top, slowly giving the spadix a somewhat rough appearance.

*Color.*—Immature: RHS 185A. Mature: RHS 184C. Ages to: RHS 181B.

Flowers:

*Quantity per spadix.*—80 to 110.

*Spadix flower arrangement.*—Bisexual, rounded in cross-section.

*Shape.*—Rounded.

*Size.*—Length: 0.05 cm to 0.10 cm. Diameter (maximum): 0.10 cm.

*Color.*—RHS 158B.

Reproductive organs:

*Stamens.*—Not visible.

*Pollen amount.*—Absent.

*Pistil.*—Quantity: 80 to 110. Length: Less than 0.01 cm. Color: RHS 158B.

*Style.*—Not observed to date.

*Stigma.*—Shape: Ovoid. Diameter: Less than 0.01 cm. Color: RHS 158B.

*Ovary.*—Rarely visible.

*Ovary color.*—Not measured.

Fruit and seed set: None observed to date.

Disease and pest resistance: No specific resistance or susceptibility observed to pathogens or pests common to *Anthurium* under commercial conditions to date.

COMPARISON WITH PARENTAL AND SIMILAR COMMERCIAL VARIETIES

'AN2884386' differs from the female parent plant '12870-01' (unpatented) in that 'AN2884386' has white, orbicular-cordate spathes, and venation color of mature leaves is red at the base and green towards the tips, whereas '12870-01' has light pink, cordate spathes, and venation color of mature leaves is green.

'AN2884386' differs from the male parent plant 'ANTHIFOFUN' (U.S. Plant Pat. No. 30,527) in that 'AN2884386' has white, orbicular-cordate spathes, and angle of the distal part of the spathe to the peduncle is approximately a right angle, whereas 'ANTHFOFUN' has pink, broad-cordate spathes, and the angle of the distal part of the spathe to the peduncle is acute.

'AN2884386' differs from similar commercial variety 'ANTHFAXI' (U.S. Plant Pat. No. 30,112) in that 'AN2884386' has orbicular-cordate spathes that are positioned slightly above the leaves, strong peduncle anthocyanin coloration, and short, purplish-red spadices with red tips, whereas 'ANTHFAXI' has cordate spathes that are positioned at the same level to slightly above the leaves, weak peduncle anthocyanin coloration, and very short to short, red spadices with red tips.

'AN2884386' differs from similar variety 'ANTHGLAM' (U.S. Plant Pat. No. 33,771) in that 'AN2884386' has white, orbicular-cordate spathes, purplish-red spadices with red tips and leaf lobes, whereas 'ANTHGLAM' has pink, ovate spathes, red spadices with red tips and absent of leaf lobes.

I claim:

1. A new and distinct variety of *Anthurium* plant named 'AN2884386', substantially as illustrated and described herein.

* * * * *